United States Patent [19]

Schnurbusch et al.

[11] Patent Number: 4,544,402
[45] Date of Patent: Oct. 1, 1985

[54] 4-DL-ALKYLESTER-α-ALANINYL-6-CHLORO-S-TRIAZINES AND THE USE THEREOF AS HERBICIDES

[75] Inventors: Horst Schnurbusch, Herne; Helmut Baltruschat, Nottuln, both of Fed. Rep. of Germany

[73] Assignee: Chemische Werke Huls Aktiengesellschaft, Marl, Fed. Rep. of Germany

[21] Appl. No.: 613,781

[22] Filed: May 24, 1984

[30] Foreign Application Priority Data

Jun. 24, 1983 [DE] Fed. Rep. of Germany ....... 3322720

[51] Int. Cl.$^4$ .................... C07D 251/50; A01N 43/70
[52] U.S. Cl. ........................................ 71/93; 544/204; 544/208
[58] Field of Search ..................... 71/93; 544/204, 208

[56] References Cited

U.S. PATENT DOCUMENTS

| 3,629,259 | 12/1971 | Schwarzee ........................ 544/204 |
| 3,856,793 | 12/1974 | MacDonarld ..................... 544/204 |
| 4,007,032 | 2/1977 | Berrer ............................... 544/204 |
| 4,104,040 | 8/1978 | Oi et al. ............................. 55/67 |

FOREIGN PATENT DOCUMENTS 2238042  2/1973  Fed. Rep. of Germany ...... 544/204

OTHER PUBLICATIONS

Oi et al., Chemical Abstracts, vol. 90, Entry 152563g (1979).
Oi et al., Chemical Abstracts, vol. 89, Entry 129543w (1978).
Kuehne et al., Chemical Abstracts, vol. 86, Entry 121378p (1977).
Ohi et al., Chemical Abstracts, vol. 86, Entry 37316j (1977).
Dovlatyan et al., Chem. Abs., vol. 79, Entry 126456c (1973).
Kuehne et al., Chem. Abst., vol. 78, Entry 111373d (1973).

*Primary Examiner*—John M. Ford
*Attorney, Agent, or Firm*—Oblon, Fisher, Spivak, McClelland & Maier

[57] ABSTRACT

4-DL-alkylester-γ-alaninyl-6-chloro-S-triazines having the formula (I):

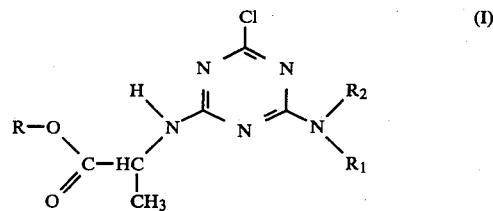

wherein $R_1$ is a straight or branched chain alkyl, alkoxy, alkoxyalkyl or alkylol radical which is unsubstituted or substituted by a cyclopentyl or cyclohexyl group, which is, itself, unsubstituted or substituted by up to 5 methyl groups; $R_2$ is a radical from the group of alkyl radicals of 1 to about 3 carbon atoms, or a hydrogen atom; and R is a radical from the group of alkyl radicals of 1 to about 3 carbon atoms.

10 Claims, No Drawings

4-DL-ALKYLESTER-α-ALANINYL-6-CHLORO-S-TRIAZINES AND THE USE THEREOF AS HERBICIDES

BACKGROUND OF THE INVENTION

1. Field of the Invention

This invention relates to 4-DL-alkyl ester-α-alaninyl-6-chloro-s-triazines and their use as herbicides, particularly against wild oats.

2. Description of the Prior Art

2-Chloro-4,6-bis(ethylamino)-1,3,5-trizaine (simazine, cf. CH-PS No. 329 277 and CH-PS No. 342 784 or DE-AS 10 11 904) and 2-chloro-4-ethylamino-6-isopropylamino-1,3,5-triazine (atrazine, cf DE-AS No. 10 11 904) are representative of the chloro-1,3,5-triazines, which from the mid-1960s until now have had the broadest use in controlling weeds and harmful grasses in various cultivated plants.

A disadvantage of the chloro-s-triazines, which have been known and used so far, has generally been their general action, i.e., not only the harmful grasses but also useful plants are damaged by their use. At any rate, very specific selectivities have been observed with individual s-triazine derivatives, for example, those of the above mentioned compounds in corn, sugar cane or pineapple. However, herbicides from this class, or other classes of substances, which exhibit selectivity with respect to winter wheat, oats, barley, wheat, rape, rice or sugar beets, for example, are unknown.

Therefore, a need clearly continues to exist for herbicidal compositions which exhibit a selective action against weeds and harmful grasses in the presence of grain crops such as wheat, barley or rye, without damaging these crops.

SUMMARY OF THE INVENTION

Accordingly, it is an object of the present invention to provide herbicidal compositions which exhibit a selective action against weeds and harmful grasses in the presence of grain crops such as wheat, barley or rye, without damaging these crops.

It is also an object of this invention to provide a herbicidal composition which, in particular, exhibits a selective action against wild oats in the presence of grain crops such as wheat, barley or rye without damaging these crops.

Moreover, it is also an object of the present invention to provide a process for the use of the present compounds as herbicidal compositions which exhibit a selective action against weeds and harmful grasses in the presence of grain crops such as wheat, barley or rye, without damaging these crops.

According to the present invention, the foregoing and other objects are attained by providing 4-DL-alkyl ester-α-alaninyl-6-chloro-s-triazines having the formula (I):

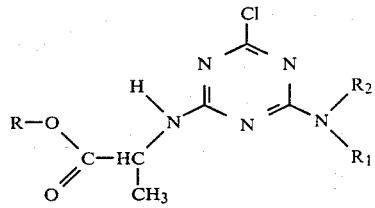

wherein $R_1$ is a straight or branched chain alkyl, alkoxy, alkoxy alkyl or alkylol radical which is unsubstituted or substituted by a cyclopentyl or cyclohexyl group, which is, itself, unsubstituted or substituted by up to 5 methyl groups; $R_2$ is a radical from the group of alkyl radicals of 1 to about 3 carbon atoms, or a hydrogen atom; and R is a radical from the group of alkyl radicals of 1 to about 3 carbon atoms.

DETAILED DESCRIPTION OF THE PREFERRED EMBODIMENTS

It is, indeed, surprising that the mixed substitution of the chloro-s-triazines with a straight or branched chain or cycloaliphatic amine and an alanine ester yields compounds exhibiting excellent selective action against weeds and harmful grasses in the presence of wheat, barley and rye, without damaging these crops. In particular, the compounds of the present invention display excellent selective action against wild oats in the presence of grain crops, without damaging the grain crops.

The excellent action against wild oats is especially remarkable with this group of substances. Because of their botanical relationship to cultivated oats and also to barley, wheat and rye, wild oats are known to be particularly difficult to control in grain crops. Wild oats cause a considerable problem in many grain habitats, since wild oats mature faster than useful grains and some of their seeds therefore get into the ground before the grain harvest. Moreover, it is difficult to separate wild oat seeds from the grain seeds during seed cleaning. Unfortunately, s-triazines having a good action against wild oats and with a simultaneous selectivity in grain crops such as wheat, barley and rye and especially cultivated oats, are unknown.

The compounds according to the invention which exhibit a surprisingly good selectivity in grains and have a simultaneously good action against wild oats, therefore represent a valuable addition to the herbicides for selective weed control.

In contrast with alanine derivatives that have become known in the literature, as a suffix (=2(N-benzoyl-3,1-dichloropenylamino)propionic acid ethyl ester cf DE-PS No. 16 13 527), the compounds according to the invention offer the advantage of having the known broad action of triazines against weeds and other harmful grasses (other than wild oats).

Besides their very good compatibility with grains, the compounds according to the invention are remarkable with a broad selectivity spectrum toward a great number of other cultivated plants. These compounds are selective in soybeans, cotton and rice (Latin names given in Table 2) before and/or after germination.

The uses of these compounds according to the invention is not limited to crops of the types of the plants named above, but can also be successfully applied to other plant crops.

Depending on the concentration, the compounds can also be used for complete weed control, e.g., on industrial and rail sites or on roads and grounds with or without trees. The compounds according to the invention are also suitable for weed control in perennial crops, e.g., forest, ornamental wood, fruit, vineyard, citrus, nut, banana, coffee, tea, rubber, oil palm, cacao, berry and hops areas.

In the case of some types of plants, the compounds according to the invention act to inhibit the length of growth but without resulting in a reduction in yield. For this reason, they can further be used as a growth regulating agent. Some of the new compounds can also be used as dofoliants, desiccants, weed killing and sprout inhibiting agents.

The invention also relates to the use of 4-DL-alkyl ester-α-alaninyl-6-chloro-s-triazines substituted in the 2 position with a (substituted) amino group of the general formula (I):

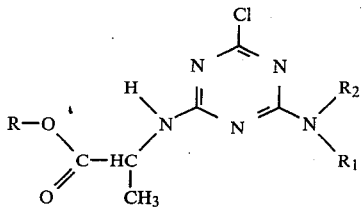

where $R_1$ is a straight or branched chain alkyl, alkoxy, alkoxyalkyl or alkylol radical or, optionally, a cyclopentyl or cyclohexyl ring substituted with up to 5 methyl groups, $R_2$ is a radical from the group of alkyls with one to three C atoms or preferably an H atom, R is a radical from the group of alkyls with one to three C atoms, in a form suitable for application for selective treatment of useful plant crops with a broad spectrum of action against weeds and harmful grasses before and/or after germination of the seeds.

PRODUCTION OF RACEMATES ACCORDING TO THE INVENTION

Production occurs, omitting the commonplace neutralizing reactions with NaOH of the HCl released after steps 1 and 2, as follows:

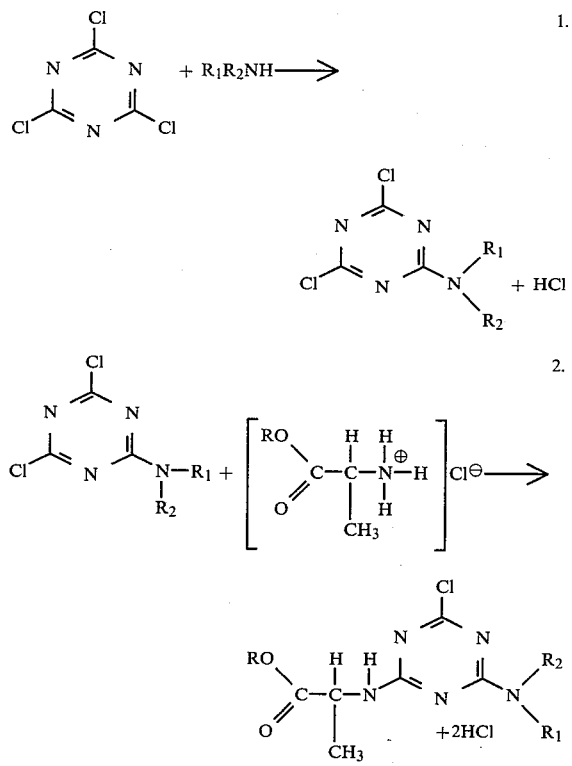

The symbols $R_1$, $R_2$ and R have the meanings given above for formula I. Then the solvents used are separated by distillation and the resulting common salt is removed by washing until freedom from chloride is indicated.

The yield, relative to the cyanuric chloride, is 85 to 92%.

Since with α-alanine esters, the carbon atom next to the COOR group is asymmetric, the reaction products of these compounds with s-triazines are always racemates.

The names of the racemates produced are in Table 1a and the substituents $R_1$, $R_2$ and R and their melting ranges are given in Table 1b. In the tables, racemates 1 to 18 relate to 4-DL-ethyl ester-α-alaninyl-6-chloro-s-triazine derivatives and racemates 101 to 118 the corresponding 4-DL-isopropyl ester-α-alaninyl-6-chloro-s-triazine derivatives.

The present invention will be further illustrated by certain examples and references which are provided for purposes of illustration only and are not intended to limit the present invention. It will also be seen that the general details of compound production can be taken or derived from the following examples for an ethyl ester and an isopropyl ester derivative. Only insignificant changes in the reaction temperatures and times, yields and further processings occur with other amines.

EXAMPLE 1

Racemate 2

Production of 2-methylamino-4-DL-ethyl ester-α-alaninyl-60-chloro-s-triazine 184.5 g (1.00 mole) of cyanuric chloride are dissolved in 900 ml of acetone and added drop by drop with vigorous stirring in 1100 ml of water at 0° to 2° C. for 30 min. 31.0 g (1.00 mole) of methylamine as a 30% aqueous solution also with vigorous stirring are then added drop by drop in the resulting suspension in 30 min at 0° to 2° C. The batch is further stirred for 30 min. Thus, the product remains largely undissolved. The batch is a suspension that can be stirred well during the reaction with methylamine and neutralization of the separated HCl with NaOH.

The 40.0 g (1.00 mole) of NaOH needed for neutralization are added drop by drop as a 30% solution in 60 min at 0° to 2° C. with vigorous stirring. The pH value should not exceed 8.0; it reaches 8.5 to 9.0 only toward the end of neutralization.

For further reaction 168.9 g (=1.10 mole) of DL-alanine ethyl ester hydrochloride in the form of a 30% ethyl alcohol solution are added drop by drop at −5° C. in 30 min with vigorous stirring.

Then, 1.10 mole of NaOH as a 30% solution is added at −5° C. in 60 min to neutralize the hydrochloride. The suspension is then heated to 25° to 30° C. in 60 min with stirring and mixed with another 1.00 mole of 30% NaOH at this temperature. Neutralization takes 6 h, during which the pH value of 8.0 should not be exceeded and reaches a value of 9.0 only toward the end.

For further processing, acetone and alcohol are distilled off the batch, the white crystalline product is suctioned off and washed free of chloride with water. After drying in vacuo at 50° C., the yield, relative to the cyanuric chloride used, is 89%.

EXAMPLE 2

Racemate 115

Production of 2-cyclopentylamino-4-DL-isopropyl ester-α-alaninyl-6-chloro-s-triazine 184.5 g (1.00 mole) of cyanuric chloride are dissolved in 900 ml of acetone and added drop by drop to 1,100 ml of water at 0° to 2° C. in 30 min with vigorous stirring. Then 85.0 g (1.00 mole) of cyclopentylamine are added drop by drop to the resulting suspension in 30 min at 0° to 2° C. also with vigorous stirring. The batch is stirred for another 30 min, during which the suspended product for the most part goes into solution.

Then 40.0 g (1.00 mole) of NaOH as a 30% solution are added drop by drop in 30 min to neutralize the separated HCl. The pH value 8.0 should not be exceeded; it should reach a value of 8.5 to 9.0 only toward the end of neutralization. The batch is vigorously stirred and the temperature kept at 0° to 2° C. During addition of the NaOH, the product again precipitates out finely divided and is a suspension that can be stirred well.

After the completion of addition of the NaOH, 184,4 g (1.10 mole) of DL-alanine-isopropyl ester hydrochloride is added drop by drop as a 30% ethyl alcohol solution at −5° C. in 30 min with vigorous stirring.

Neutralization of the hydrochloride then occurs by adding 146.7 g (1.10 mole) of 30% NaOH drop by drop at the same temperature with vigorous stirring in a period of 60 min. The batch then contains no solid product; a part of the product separates as an organic layer on the aqueous solution. Then it is heated to 25° to 30° C. in a period of 60 min with vigorous stirring and mixed at this temperature with another 133.3 g (1.00 mole) of 30% NaOH. Neutralization takes 6 hours during which the pH value of 8.0 should not be exceeded and may reach a pH value of 9.0 only toward the end.

TABLE 1a

| Names of racemates produced | Compound with... = ethyl = No. | = isopropyl = No. |
|---|---|---|
| 2-Amino-4-DL-... ester alaninyl-6-chloro-s-triazine | 1 | 101 |
| 2-Methylamino-4-DL-... ester alaninyl-6-chloro-s-triazine | 2 | 102 |
| 2-Dimethylamino-4-DL-... ester alaninyl-6-chloro-s-triazine | 3 | 103 |
| 2-Ethylamino-4-DL-... ester alaninyl-6-chloro-s-triazine | 4 | 104 |
| 2-Isopropylamino-4-DL-... ester alaninyl-6-chloro-s-triazine | 5 | 105 |
| 2-n-Propylamino-4-DL-... ester alaninyl-6-chloro-s-triazine | 6 | 106 |
| 2-tert.Butylamino-4-DL-... ester alaninyl-6-chloro-s-triazine | 7 | 107 |
| 2-2'Hydroxy-ethylamino-4-DL-... ester alaninyl-6-chloro-s-triazine | 8 | 108 |
| 2-2'Methoxy-ethylamino-4-DL-... ester alaninyl-6-chloro-s-triazine | 9 | 109 |
| 2-3'Methoxy-propylamino-4-DL-... ester alaninyl-6-chloro-s-triazine | 10 | 110 |
| 2-3'Ethoxy-propylamino-4-DL-... ester alaninyl-6-chloro-s-triazine | 11 | 111 |
| 2-3'n-Butoxy-propylamino-4-DL-... ester alaninyl-6-chloro-s-triazine | 12 | 112 |
| 2-3'n-Hexoxy-propylamino-4-DL-... ester alaninyl-6-chloro-s-triazine | 13 | 113 |
| 2-3'Isopropoxy-propylamino-4-DL-... ester alaninyl-6-chloro-s-triazine | 14 | 114 |
| 2-Cyclopentylamino-4-DL-... ester alaninyl-6-chloro-s-triazine | 15 | 115 |
| 2-Cyclohexylamino-4-DL-... ester alaninyl-6-chloro-s-triazine | 16 | 116 |
| 2-TMCPamino-4-DL-... ester alaninyl-6-chloro-s-triazine(+) | 17 | 117 |
| 2-TMCamino-4-DL-... ester alaninyl-6-chloro-s-triazine(++) | 18 | 118 |

(+)TMCP is 2,2,4- or 2,4,4-trimethylcyclopentyl-
(++)TMC is 3,3,5-trimethylcyclohexyl- TABLE 1b List of 4-DL-alkyl ester-α-alaninyl-6-chloro-s-triazine racemates with various substituents $R_1$, $R_2$ and R, R' and their melting ranges.

| | | Compound with R = ethyl | | Compound with R = isopropyl | |
|---|---|---|---|---|---|
| $R_2$ | $R_1$ | No | Melting range °C. | No | Melting range °C. |
| H | —H | 1 | 112–117 | 101 | 146–151 |
| H | —CH$_3$ | 2 | 115–120 | 102 | 156–161 |
| CH$_3$ | —CH$_3$ | 3 | 120–125 | 103 | 158–163 |
| H | —C$_2$H$_5$ | 4 | 120–125 | 104 | 135–140 |
| H | —CH(CH$_3$)$_2$ | 5 | 101–106 | 105 | 103–108 |
| H | —CH$_2$—CH$_2$—CH$_3$ | 6 | 117–122 | 106 | 127–132 |
| H | —C(CH$_3$)$_3$ | 7 | 104–109 | 109 | 80–85 |
| H | —CH$_2$—CH$_2$OH | 8 | 20–25 | 108 | 30–35 |
| H | —CH$_2$—CH$_2$OCH$_3$ | 9 | 20–25 | 109 | 120–125 |
| H | —CH$_2$—CH$_2$—CH$_2$—OCH$_3$ | 10 | 22–27 | 110 | 123–128 |
| H | —CH$_2$—CH$_2$—CH$_2$OC$_2$H$_5$ | 11 | 25–30 | 111 | 128–133 |
| H | —CH$_2$—CH$_2$—CH$_2$OCH$_2$CH$_2$CH$_2$CH$_3$ | 12 | 28–33 | 112 | 130–135 |
| H | —CH$_2$—CH$_2$—CH$_2$OCH$_2$CH$_2$CH$_2$CH$_2$CH$_2$CH$_3$ | 13 | 30–35 | 113 | 133–138 |
| H | —CH$_2$—CH$_2$—CH$_2$—O—CH(CH$_3$)$_2$ | 14 | 42–47 | 114 | 130–135 |
| H |  | 15 | 49–56 | 115 | 45–50 |
| H | 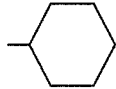 | 16 | 68–73 | 116 | 57–62 |

TABLE 1b-continued

List of 4-DL-alkyl ester-α-alaninyl-6-chloro-s-triazine racemates with various substituents R₁, R₂ and R, R' and their melting ranges.

| R₂ | R₁ | Compound with R = ethyl | | Compound with R = isopropyl | |
|---|---|---|---|---|---|
| | | No | Melting range °C. | No | Melting range °C. |
| H |  | 17 | 100–105 | 117 | 138–143 |
| H |  | 18 | 121–126 | 118 | 145–150 |

For further processing, acetone and ethyl alcohol are distilled from the batch, during which the product is separated from the remaining aqueous solution as a tacky resin. After several washings with water at 30° to 40° C. and drying in vacuo at 40° C., the yield is 88%, relative to the cyanuric chloride used.

APPLICATION OF THE ACTIVE INGREDIENTS

The active ingredients of the compounds according to the invention can be applied, depending on the crop, in an amount of about 0.125 to 10 kg/ha, preferably about 0.5 to 2.5 kg/ha. Racemates corresponding to a formula (compounds with a value for $R_1$, $R_2$ and R) and also mixtures of compounds according to the invention (i.e., those with various meanings for $R_1$ and/or $R_2$ and/or R) can be used to control weeds and harmful grasses.

It is further customary to add one or more auxiliary agents from the group of supports, diluents, solvents, wetting agents, adhesives, dispersants and emulsifiers to the active ingredients during application.

Mixing of other herbicides or use at the same time of fungicides, insecticides, growth regulators, etc., with the active ingredients or mixtures of the active ingredients according to the invention are also possible.

Finally, the active ingredients or mixtures of the active ingredients according to the invention can optionally be added to one or more representatives of the group of substances mentioned above, mineral or artificial fertilizers or soil conditioners and be spread with them.

Before germination, the application is made on the surface before the seeds sprout and after germination it is made on the leaf surface in the second to third leaf stage.

SERIES OF GREENHOUSE TESTS WITH 4, 3 AND 2 KG/HA

For most of the compounds according to the invention greenhouse tests were conducted with use of 4, 3 and 2 kg/ha, relative to the pure active ingredient, with the test plants listed in Table 2 (with their English and Latin names).

In this case, the amounts of active ingredient were suspended in 1,000 l of water/ha. An appraisal was made every 3 weeks after treatment of the crops with the active ingredient. Evaluation of the test results was made with the usual grading, in which 1 = complete action = killing of the plants and
5 = no action = plants as though untreated Tables 3 and 4 give the results only for racemates No. 4, 104 and 105 and for comparison substances 1 or 2, which are comparison substance 1 = atrazine = 2-ethylamino-3-isopropylamino-6-chloro-1,3,5-triazine and
comparison substance 2 = suffix = 2(N-benzoyl-3,4-dichlorophenylamino)-propionic acid ethyl ester.

TABLE 2

| Botanical names of test plants | |
|---|---|
| English | Latin |
| Blackgrass | *Alopecurus myosuroides* |
| Cotton | *Gossypium herbaceum* |
| Wild oat | *Avena fatua* |
| Barley | *Hordeum vulgare* |
| Cultivated oat | *Avena sativa* |
| Camomile | *Matricaria maritima* |
| Corn | *Zea mays* |
| Soybeans | *Glycin max* |
| Dead nettle | *Lamium purpureum* |
| Tomato | *Lycopersicum esculentum* |
| Chickweed | *Stellaria media* |
| Lambsquarters | *Chenopodium album* |
| Wheat | *Triticum aestivum* |
| Windgrass | *Apera spica-venti* |
| Winter rape | *Brassica napus* |

TABLE 3

Herbicidal action of compounds according to the invention used in amounts of 4, 3, 2 kg of active ingredient/ha. Application before germination of the plants.

| Test plants | Example 4 | | | Example 5 | | | Example 104 | | | Example 105 | | | Comparison means | | |
|---|---|---|---|---|---|---|---|---|---|---|---|---|---|---|---|
| | 4 | 3 | 2 | 4 | 3 | 2 | 4 | 3 | 2 | 4 | 3 | 2 | 4 | 3 | 2 |
| Winter rape | 4 | 4 | 4 | 5 | 5 | 5 | 4 | 4 | 4 | 4 | 4 | 4 | 1 | 1 | 1 |
| Tomato | 1 | 3 | 3 | 5 | 5 | 5 | 1 | 1 | 1 | 3 | 3 | 4 | 1 | 1 | 1 |
| Cultivated oat | 3 | 3 | 5 | 5 | 5 | 5 | 3 | 3 | 4 | 3 | 3 | 4 | 1 | 1 | 1 |
| Wild oar | 1 | 2 | 2 | 3 | 4 | 4 | 1 | 3 | 3 | 4 | 4 | 4 | 1 | 1 | 1 |
| Blackgrass | 1 | 1 | 1 | 3 | 3 | 5 | 1 | 1 | 1 | 1 | 1 | 2 | 1 | 1 | 1 |
| Windgrass | 1 | 1 | 1 | 3 | 3 | 3 | 1 | 1 | 1 | 1 | 1 | 1 | 1 | 1 | 1 |
| Dead nettle | 1 | 1 | 1 | 3 | 3 | 4 | 1 | 1 | 1 | 1 | 1 | 1 | 1 | 1 | 1 |
| Chickweed | 1 | 1 | 1 | 5 | 5 | 5 | 1 | 1 | 1 | 1 | 1 | 1 | 1 | 1 | 1 |
| Camomile | 1 | 1 | 1 | 4 | 5 | 5 | 1 | 1 | 1 | 1 | 1 | 1 | 1 | 1 | 1 |
| Lambsquarters | 1 | 1 | 1 | 4 | 5 | 5 | 1 | 1 | 1 | 1 | 1 | 1 | 1 | 1 | 1 |
| Barley | 5 | 5 | 5 | 5 | 5 | 5 | 5 | 5 | 5 | 5 | 5 | 5 | 1 | 1 | 1 |

TABLE 3-continued

Herbicidal action of compounds according to the invention used in amounts of 4, 3, 2 kg of active ingredient/ha. Application before germination of the plants.

| Test plants | Example 4 | | | Example 5 | | | Example 104 | | | Example 105 | | | Comparison means | | |
|---|---|---|---|---|---|---|---|---|---|---|---|---|---|---|---|
| | 4 | 3 | 2 | 4 | 3 | 2 | 4 | 3 | 2 | 4 | 3 | 2 | 4 | 3 | 2 |
| Wheat | 5 | 5 | 5 | 5 | 5 | 5 | 5 | 5 | 5 | 5 | 5 | 5 | 1 | 1 | 1 |
| Soybean | 5 | 5 | 5 | 5 | 5 | 5 | 5 | 5 | 5 | 5 | 5 | 5 | 1 | 1 | 1 |
| Cotton | 5 | 5 | 5 | 5 | 5 | 5 | 5 | 5 | 5 | 5 | 5 | 5 | 2 | 2 | 3 |
| Corn | 5 | 5 | 5 | 5 | 5 | 5 | 5 | 5 | 5 | 5 | 5 | 5 | 5 | 5 | 5 |

TABLE 4

Herbicidal action of compounds according to the invention used in amounts of 4, 3 and 2 kg of active ingredient/ha. Application after germination the plants.

| Test plants | Example 4 | | | Example 5 | | | Example 104 | | | Example 105 | | | Comparison means 1 | | | Comparison means 2 | | |
|---|---|---|---|---|---|---|---|---|---|---|---|---|---|---|---|---|---|---|
| | 4 | 3 | 2 | 4 | 3 | 2 | 4 | 3 | 2 | 4 | 3 | 2 | 4 | 3 | 2 | 4 | 3 | 2 |
| Winter rape | 1 | 1 | 3 | 1 | 1 | 1 | 1 | 1 | 1 | 1 | 1 | 4 | 1 | 1 | 1 | 5 | 5 | 5 |
| Tomato | 1 | 1 | 3 | 5 | 5 | 5 | 1 | 4 | 4 | 3 | 3 | 4 | 1 | 1 | 1 | 5 | 5 | 5 |
| Cultivated oat | 3 | 3 | 4 | 3 | 3 | 4 | 3 | 3 | 4 | 3 | 3 | 3 | 1 | 1 | 1 | 3 | 3 | 3 |
| Wild oat | 1 | 1 | 1 | 1 | 1 | 1 | 1 | 1 | 1 | 1 | 1 | 1 | 1 | 1 | 1 | 1 | 1 | 1 |
| Blackgrass | 1 | 1 | 1 | 1 | 1 | 1 | 1 | 1 | 1 | 1 | 1 | 1 | 1 | 1 | 1 | 1 | 1 | 1 |
| Windgrass | 1 | 1 | 1 | 1 | 1 | 1 | 1 | 1 | 1 | 1 | 1 | 1 | 1 | 1 | 1 | 1 | 1 | 2 |
| Dead nettle | 1 | 1 | 1 | 1 | 1 | 1 | 1 | 1 | 1 | 1 | 1 | 1 | 1 | 1 | 1 | 5 | 5 | 5 |
| Chickweed | 1 | 1 | 1 | 1 | 1 | 1 | 1 | 1 | 1 | 1 | 1 | 1 | 1 | 1 | 1 | 5 | 5 | 5 |
| Camomile | 1 | 1 | 1 | 1 | 2 | 3 | 1 | 1 | 1 | 1 | 1 | 1 | 1 | 1 | 1 | 5 | 5 | 5 |
| Lambsquarters | 1 | 1 | 1 | 1 | 3 | 3 | 1 | 1 | 1 | 1 | 1 | 1 | 1 | 1 | 1 | 3 | 5 | 5 |
| Barley | 4 | 4 | 5 | 4 | 4 | 5 | 3 | 4 | 5 | 3 | 4 | 4 | 1 | 1 | 1 | 4 | 5 | 5 |
| Wheat | 4 | 4 | 5 | 3 | 4 | 5 | 4 | 4 | 5 | 3 | 4 | 4 | 1 | 1 | 1 | 5 | 5 | 5 |
| Soybean | 5 | 5 | 5 | 5 | 5 | 5 | 5 | 5 | 5 | 5 | 5 | 5 | 1 | 1 | 1 | 5 | 5 | 5 |
| Cotton | 5 | 5 | 5 | 5 | 5 | 5 | 5 | 5 | 5 | 5 | 5 | 5 | 1 | 1 | 1 | 5 | 5 | 5 |
| Corn | 5 | 5 | 5 | 5 | 5 | 5 | 5 | 5 | 5 | 5 | 5 | 5 | 5 | 5 | 5 | 5 | 5 | 5 |

The results in Tables 3 and 4 show that the compounds according to the invention both before and after germination exhibit an excellent action against numerous weeds and harmful grasses such as wild oat, blackgrass, windgrass, dead nettle, chickweed, camomile and lambsquarters. In their case the selectivity in various crops, such as barley, wheat, cultivated oats, soybean, cotton, is considerably better than in the case of comparison means 1 (atrazine). In contrast with comparison means 2 (suffix) which represents the state of the art as a wild oat herbicide, there is a substantially broadened spectrum of action against dicotyledonous weeds.

In cultivated oat crops, the racemates according to the invention had to be used in an amount under 2 kg/ha, since otherwise some damage to the useful plants would have been observed.

SERIES OF GREENHOUSE TESTS WITH USE OF 1, 0.5, 0.25 AND 0.125 KG/HA AFTER GERMINATION

Because of the great herbicidal action of the compounds according to the invention, still smaller amounts (1, 0.5, 0.25 and 0.125 g active ingredient/ha) were tested after germination.

According to Table 5 the action of the compounds according to the invention against wild oats is equal to the comparison means 2. However, the spectrum of action of the compounds according to the invention is clearly greater than this comparison means. In comparison with s-triazines, such as comparison means 1, the crop selectivity in grain types (barley, wheat) also after germination is given, so that, in contrast with comparison means 1, the compounds according to the invention can be used for control of wild oats and blackgrass in grain.

TABLE 5

Herbicidal action of the compounds according to the invention used in amounts of 1, 0.5, 0.25 and 0.125 kg/ha. Application after germination of plants.

| Test plants | Example 4 | | | | Example 104 | | | | Example 105 | | | | Comparison means 1 | | | | Comparison means 2 | | | |
|---|---|---|---|---|---|---|---|---|---|---|---|---|---|---|---|---|---|---|---|---|
| | 1 | 0.5 | 0.25 | 0.125 | 1 | 0.5 | 0.25 | 0.125 | 1 | 0.5 | 0.25 | 0.125 | 1 | 0.5 | 0.25 | 0.125 | 1 | 0.5 | 0.25 | 0.125 |
| Wild oat | 1 | 1 | 1 | 1 | 1 | 1 | 1 | 2 | 1 | 1 | 1 | 2 | 1 | 1 | 1 | 1 | 1 | 1 | 1 | 2 |
| Blackgrass | 1 | 1 | 1 | 2 | 1 | 1 | 1 | 2 | 1 | 1 | 1 | 2 | 1 | 1 | 1 | 2 | 1 | 1 | 1 | 2 |
| Dead nettle | 1 | 1 | 1 | 2 | 1 | 1 | 1 | 2 | 1 | 1 | 1 | 2 | 1 | 1 | 1 | 2 | 5 | 5 | 5 | 5 |
| Chickweed | 1 | 1 | 1 | 3 | 1 | 1 | 1 | 3 | 1 | 1 | 2 | 3 | 1 | 1 | 2 | 3 | 5 | 5 | 5 | 5 |
| Camomile | 1 | 1 | 1 | 1 | 1 | 1 | 1 | 1 | 1 | 1 | 1 | 1 | 1 | 1 | 1 | 1 | 5 | 5 | 5 | 5 |
| Lambsquarters | 1 | 1 | 1 | 1 | 1 | 1 | 1 | 1 | 1 | 1 | 1 | 1 | 1 | 1 | 1 | 1 | 5 | 5 | 5 | 5 |
| Barley | 5 | 5 | 5 | 5 | 5 | 5 | 5 | 5 | 5 | 5 | 5 | 5 | 1 | 1 | 1 | 3 | 5 | 5 | 5 | 5 |
| Wheat | 5 | 5 | 5 | 5 | 5 | 5 | 5 | 5 | 5 | 5 | 5 | 5 | 1 | 1 | 1 | 2 | 5 | 5 | 5 | 5 |
| Rye | 5 | 5 | 5 | 5 | 5 | 5 | 5 | 5 | 5 | 5 | 5 | 5 | 1 | 1 | 1 | 1 | 5 | 5 | 5 | 5 |

Having now fully described this invention, it will be apparent to one of ordinary skill in the art that many changes and modifications can be made thereto without departing from the spirit or scope of the invention as set forth herein.

What is claimed is:

1. A method of selectively treating useful plant crops against weeds and harmful grasses before germination of the seeds, after germination of the seeds or before and after germination of the seeds which comprises applying one or more 4-DL-alkyl ester-α-alaninyl-6-chloro-s-triazines having the formula (1):

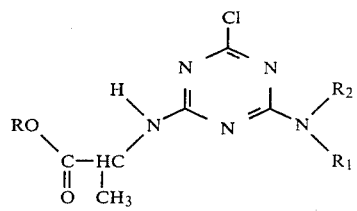

wherein $R_1$ is a radical having not more than 10 carbon atoms selected from the group of straight or branched chained alkyl, alkoxy, alkoxyalkyl or alkylol radicals which are unsubstituted, or which are substituted by a cyclopentyl or cyclohexyl group, which is itself, unsubstituted or substituted by up to five methyl groups; $R_2$ is a radical from the group of alkyl radicals of 1 to about 3 carbon atoms, or a hydrogen atom; and R is a radical from the group of alkyl radicals of 1 to about 3 carbon atoms.

2. The method of claim 1, wherein said plant crops are selectively treated against weeds and harmful grasses before germination of the seeds by applying said compound or compounds to the soil.

3. The method of claim 1, wherein said plant crops are selectively treated against weeds and harmful grasses after germination of the seeds by applying said compound or compounds to the leaf surface in the second to third leaf stages.

4. The method of claim 1, wherein said effective amount is an amount in the range of 0.125–10 kg/ha.

5. The method of claim 4, wherein said effective amount is an amount in the range of 0.5–2.5 kg/ha.

6. The method of claim 1, wherein said useful plant crops are barley, wheat, cultivated oats, soybeans and cotton.

7. The method of claim 6, wherein the treatment of cultivated oats comprises applying said composition in an amount such that the amount of the effective compound or compounds used is not in excess of about 2 kg/ha.

8. The method of claim 1, wherein said weeds and harmful grasses are wild oats, blackgrass, windgrass, dead nettle, chickweed, camomile and lambsquarters.

9. A method of selectively treating useful plant crops against weeds and harmful grasses before germination of the seeds, after germination of the seeds or before and after germination of the seeds which comprises applying a composition comprising an effective amount of one or more 4-DL-alkyl ester-α-alaninyl-6-chloro-s-triazines having the formula (I):

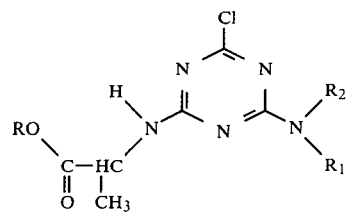

wherein $R_1$ is a radial having not more than 10 carbon atoms selected from the group of straight or branched alkyl, alkoxy, alkoxyalkyl or alkylol radicals which are unsubstituted, or which are substituted by a cyclopentyl or cyclohexyl group, which is, itself, unsubstituted or substituted by up to 5 methyl groups; $R_2$ is a radical from the group of alkyl radicals of 1 to about 3 carbon atoms, or hydrogen atoms; and R is a radical from the group of alkyl radicals of 1 to about 3 carbon atoms.

10. The method of claim 9, wherein said composition further comprises an auxiliary agent selected from the group of supports, diluents, solvents, wetting agents, adhesives, dispersants, emulsifiers; and other herbicides, fungicides, insecticides, growth regulators or fertilizers.

* * * * *